United States Patent [19]

Adams et al.

[11] Patent Number: 5,184,502
[45] Date of Patent: Feb. 9, 1993

[54] HELICOPTER INSTALLABLE, SELF-POWERED, MODULAR, REMOTE, TELEMETRY PACKAGE

[75] Inventors: George W. Adams, Newtown, Conn.; Michael J. McGoey, Fort Collins, Colo.

[73] Assignee: Remote Power, Inc., Fort Collins, Colo.

[21] Appl. No.: 716,130

[22] Filed: Jun. 17, 1991

[51] Int. Cl.$^5$ .................. G01N 1/22; H02N 6/00
[52] U.S. Cl. ...................... 73/31.01; 73/31.02; 136/244; 136/291; 136/293; 320/2; 422/83
[58] Field of Search ............ 136/244, 291, 293; 320/2; 73/31.01, 31.02; 422/83

[56] References Cited

U.S. PATENT DOCUMENTS

| | | | |
|---|---|---|---|
| 3,603,952 | 9/1971 | Smith | 340/539 |
| 4,367,633 | 1/1983 | Strathman | 62/236 |
| 4,452,234 | 6/1984 | Withjack | 126/450 |
| 4,474,028 | 10/1984 | Miller et al. | 62/235.1 |
| 4,481,562 | 11/1984 | Hickson | 362/183 |
| 4,718,185 | 1/1988 | Conlin et al. | 40/442 |

FOREIGN PATENT DOCUMENTS

| | | | |
|---|---|---|---|
| 62-13084 | 1/1987 | Japan | 136/244 |
| WO89/02055 | 3/1989 | PCT Int'l Appl. | 136/244 |

OTHER PUBLICATIONS

D. D. Faehn, *Conf. Record, 12th IEEE Photovoltaic Specialists Conf.* (1976), pp. 715-720.
J. N. Deyo et al., *Ibid*, pp. 698-704.
Y. Chevalier et al., *Conf. Record, 15th IEEE Photovoltaic Specialists Conf.* (1981), pp. 201-204.
Solarex Corp., Rockville, Md., Application Notes 6903-6904 (1977, 1978).
Amperex Electronic Corp., Slatersville Division, Product Brochure.
Solar Power Corp., Product Brochure (1978).
SES, Inc. Product Application Sheet (1977).

*Primary Examiner*—Aaron Weisstuch
*Attorney, Agent, or Firm*—F. Eugene Davis, IV

[57] ABSTRACT

The instrumentation package is transportable to remote sites solely by a light helicopter. Accordingly, three skids are provided, each of which weighs less than 1,200 pounds. An instrument skid comprises a generally, horizontally disposed frame having jacks mounted on it for leveling. Instruments and control elements are also mounted to the frame, preconnected at the factory, and protected from weather. A separate battery skid is provided which is mounted on the instrument skid at the site. A solar array skid, the sloping roof of which comprises solar cells is separately transportable by helicopter to the site and is lowered onto and fastened to the instrument skid. The instrument skid preferably has a self-contained generator mounted thereon when it is transported to the site. An instrument and antenna mounting tower for telemetry, if desired, is broken down and carried within the solar array skid to the site and then mounted on the rear of the instrument skid and tied to the solar array skid. The solar array faces the equator. The battery skid is located, such that predetermined relative wind velocities from the north or the south produce a zero force at any one jack. The solar array extends over the instruments and control elements and the generator mounted on the instrument skid. The package is particularly useful for monitoring air quality, in which case a gas analyzer is mounted on the instrument skid in a refrigerator.

10 Claims, 13 Drawing Sheets

HELICOPTER INSTALLABLE, SELF-POWERED, MODULAR, REMOTE, TELEMETRY PACKAGE

TECHNICAL FIELD

This invention relates to a helicopter installable, self-powered, modular, remote, instrumentation package. More particularly, it relates to such a package for monitoring meteorological conditions in the field, particularly including continuous gas analysis of the atmosphere. The data collected may be recorded at the site or it may be telemetered to a central location, or both.

BACKGROUND ART

Various package configurations have been utilized for remote meteorological instrumentation. These have included systems powered by gasoline or diesel powered generators, fuel cells, solar panels, and the like. It has been found extremely difficult to locate prior art instrumentation packages of this type remotely, in that, the entire package or components thereof cannot be readily transported to remote sites by light helicopter and easily assembled at the site, disassembled when desired, and removed to another site.

The United States Environmental Protection Agency has for a number of years attempted to require potential air polluters to continuously monitor certain meteorological and air gas parameters at remote sites. In particular, they want remote instrumentation packages including a continuous gas analyzer (which comprises an electrical heater, and metering and sampling pumps) in said packages.

The industry has not been able to supply such packages because of the large power consumption of such instruments, particularly the continuous gas analyzer, and the remoteness of many of such sites, they being far from utility lines, inaccessible by roads, or even when near utility lines being subject to variations in, voltage and blackouts. The use of internal combustion powered electric generators is precluded because the exhaust gases would contaminate the air quality measurements being made and transporting fuel to sites inaccessible by road is extremely expensive and cannot be relied upon under all weather conditions.

Locations range from flat desert to rocky mountain sides. Maximum temperatures exceed 105° F. and minimum temperatures well below 0° F. Winds commonly rise to as much as 85 miles an hour. On the other hand, the continuous gas analyzer requires a small ambient temperature range, approximately 75° F. plus or minus 10° F., so provision must be made to heat and cool the instrument when the ambient temperature is below or exceeds that range.

Additionally, there is a wide variation in the amount of solar power received due to weather conditions, variations between day and night, and variations between winter and summer.

As previously indicated, a collective solution to all these problems has eluded the industry to date.

DISCLOSURE OF THE INVENTION

We provide a remote, self-powered, instrumentation package neatly divided into three modular units, each of which weighs less than 1,200 pounds and can be carried to the site by helicopter. The first component is an instrument skid which comprises a generally horizontally disposed frame, and instruments and control elements mounted to the frame. The instruments include a refrigerator for enclosing the continuous gas analyzer. Jacks are provided for leveling the horizontally disposed frame. The skid also may comprise a generator which may be gasoline or diesel powered which is only used for initially charging the batteries and for repairs at the site. A second, battery skid is provided which contains the preconnected batteries which are not charged for safety and when brought in by helicopter are positioned onto the instrument skid.

We also provide a solar array skid which comprises a lean-to like structure which has a slanted array of solar cells comprising the roof portion thereof. During transport, this array also carries a meteorological array of instruments and may carry one or more radio antennae. The solar array skid is transported by helicopter and placed by helicopter upon the instrument skid over the instrument and control elements and the battery skid. The slanted solar array roof extends over the various instruments and control elements and battery skid mounted on the instrument skid and protects them from the elements. The entire unit is mounted with the solar array facing directly toward the equator.

The various elements mounted to the instrument skid, particularly, the very heavy battery skid are located, such that, predetermined north and south winds are required to just lift one of the cornered mounted jacks from the ground.

OBJECTS OF THE INVENTION

It is therefore an object of the invention to provide a helicopter installable, self-powered, modular, remote, instrumentation package.

Another object of the invention is to provide such a package which can be conveniently transported by light helicopter in three modular units.

A further object of the invention is to provide such a package including a meteorological instrument mast carried to the site within one of said three modular units and then mounted to the package at the site.

Other objects of the invention will in part be obvious and will in part appear hereinafter.

The invention accordingly comprises the features of constructions, choice of elements and parts, and arrangements of parts and elements, all of which will be exemplified in the constructions hereinafter described. The scope of the invention will be indicated in the claims.

BRIEF DESCRIPTION OF THE DRAWINGS

For a fuller understanding of the nature and objects of the invention, reference should be had to the following detailed description taken in connection with the accompanying drawings, in which.

BEST MODE FOR CARRYING OUT THE INVENTION

Figure 1:
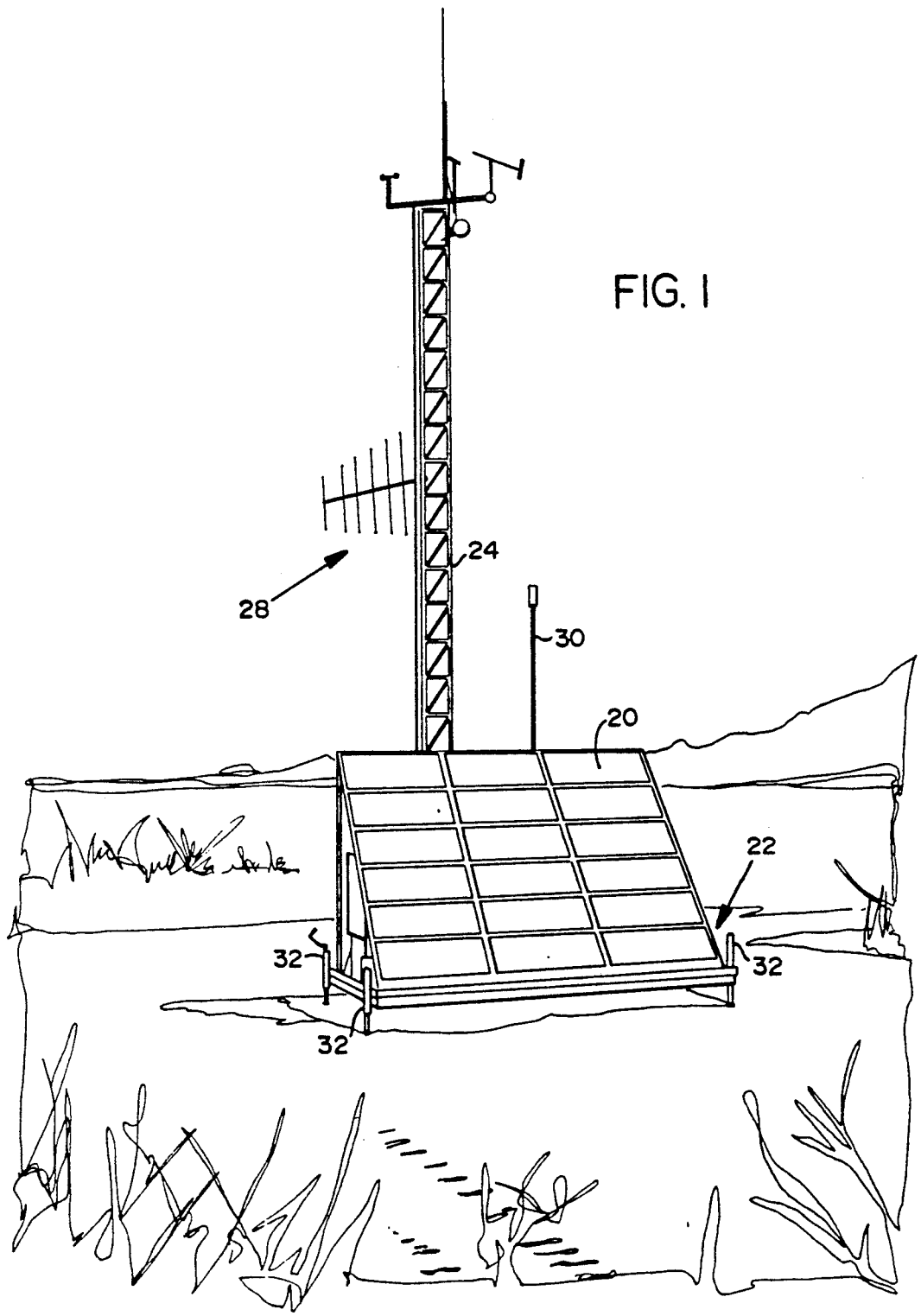
FIG. 1 is a perspective view of a remote located, self-powered, helicopter installable, modular, instrumentation package according to the invention.

Referring to FIG. 1, the solar array generally indicated at 20 is the basic power source for the helicopter installable, self-powered, modular, remote, instrumentation package of the invention which is generally indicated at 22. The solar array 20 forms the slanting roof of the package 22 and faces the equator. A vertical mast 24 is mounted to the package 22 and carries an array of meteorological instruments 26 and, if desired, a radio antenna 28. Also mounted to the package 22 is gas analyzer input pipe 30. Jacks 32 are located at the four corners of the package 22, two, of which, can be seen in FIG. 1.

Figure 2:
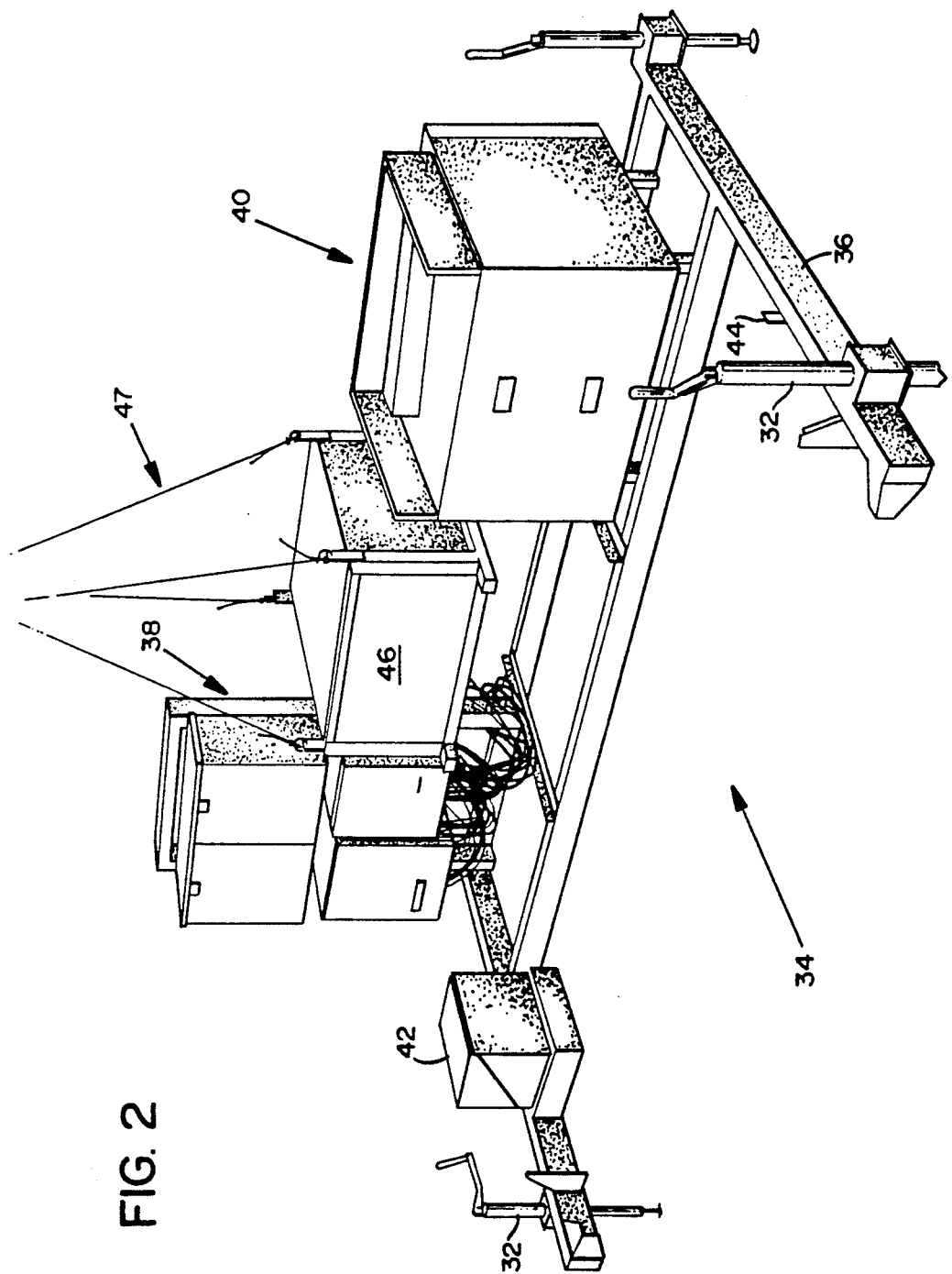
FIG. 2 is a perspective view of the instrument skid according to the invention and the battery skid according to the invention with the battery skid in the process of being mounted on the instrument skid.

FIG. 2 shows the instrument skid of the invention generally indicated at 34. It comprises a generally, horizontally disposed frame 36 with the four jacks 32 mounted at the corners thereof.

Mounted to the instrument skid 34 are control and instrument elements generally indicated at 38 and the continuous gas analyzer mounted within a refrigerator generally indicated at 40. The instrument elements may include various measuring and recording instruments and appropriate telemetry devices. Also mounted to the instrument skid 34 is a gasoline powered generator 42.

Figure 3:
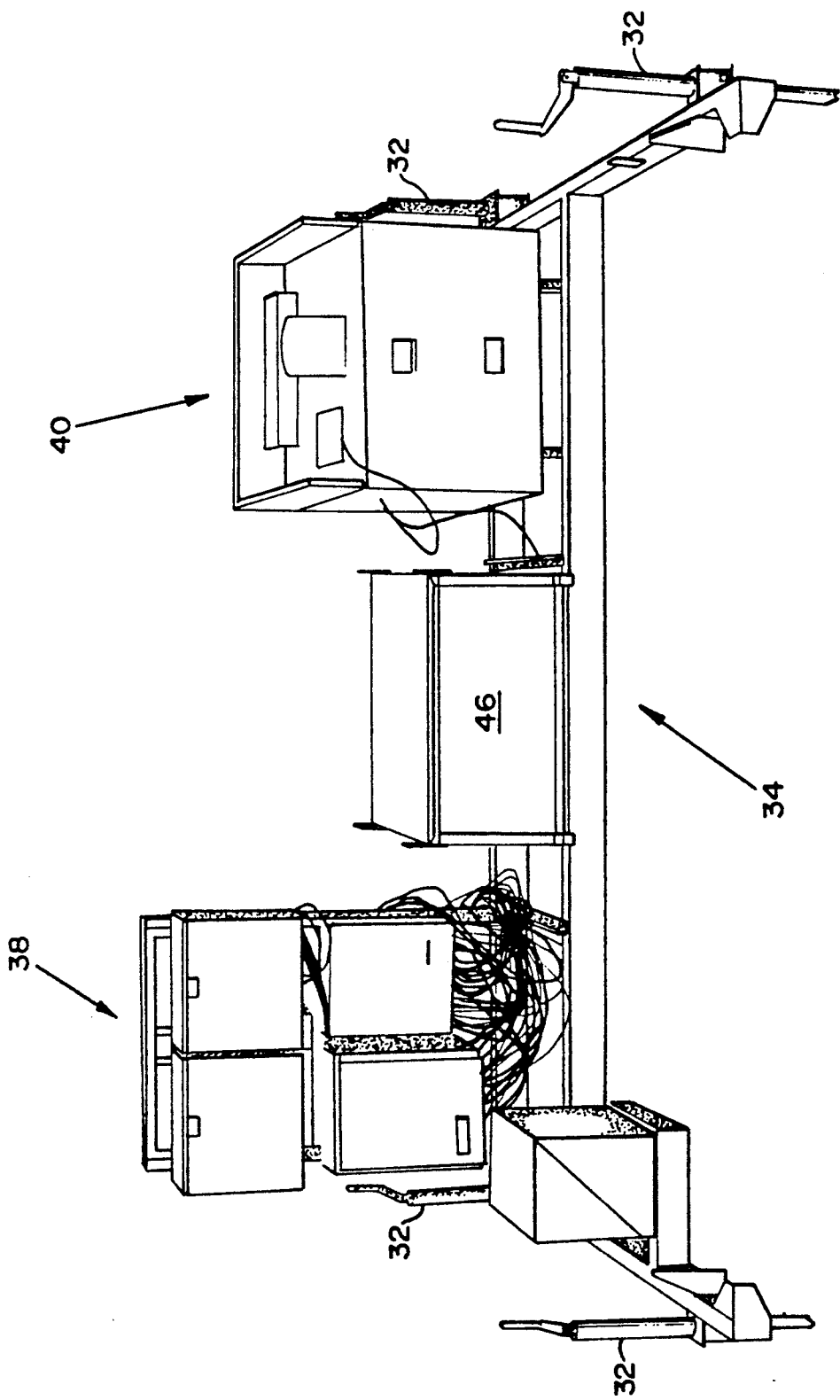
FIG. 3 is a perspective view of the instrument skid with the battery skid mounted thereon at a remote site.

The instrument skid 34 is assembled at the factory with the control and instrument elements 38 and refrigerator 40 mounted thereto and connected together by weather protected conduit or cable. The generator 42 is mounted on the instrument skid 34 and the instrument skid is then lifted via four lift eyes 44, one of which can be seen in FIG. 2. In FIG. 2, the technicians can be seen guiding the battery skid 46 onto the frame 36 of the instrument skid 34. The battery skid 46 is placed onto the instrument skid 34 suspended from a crane or helicopter by cables generally indicated at 47. In FIG. 3, the battery skid can be seen mounted to the instrument skid 34 and the remaining jacks 32 of the skid 34 can be seen.

Figure 4:
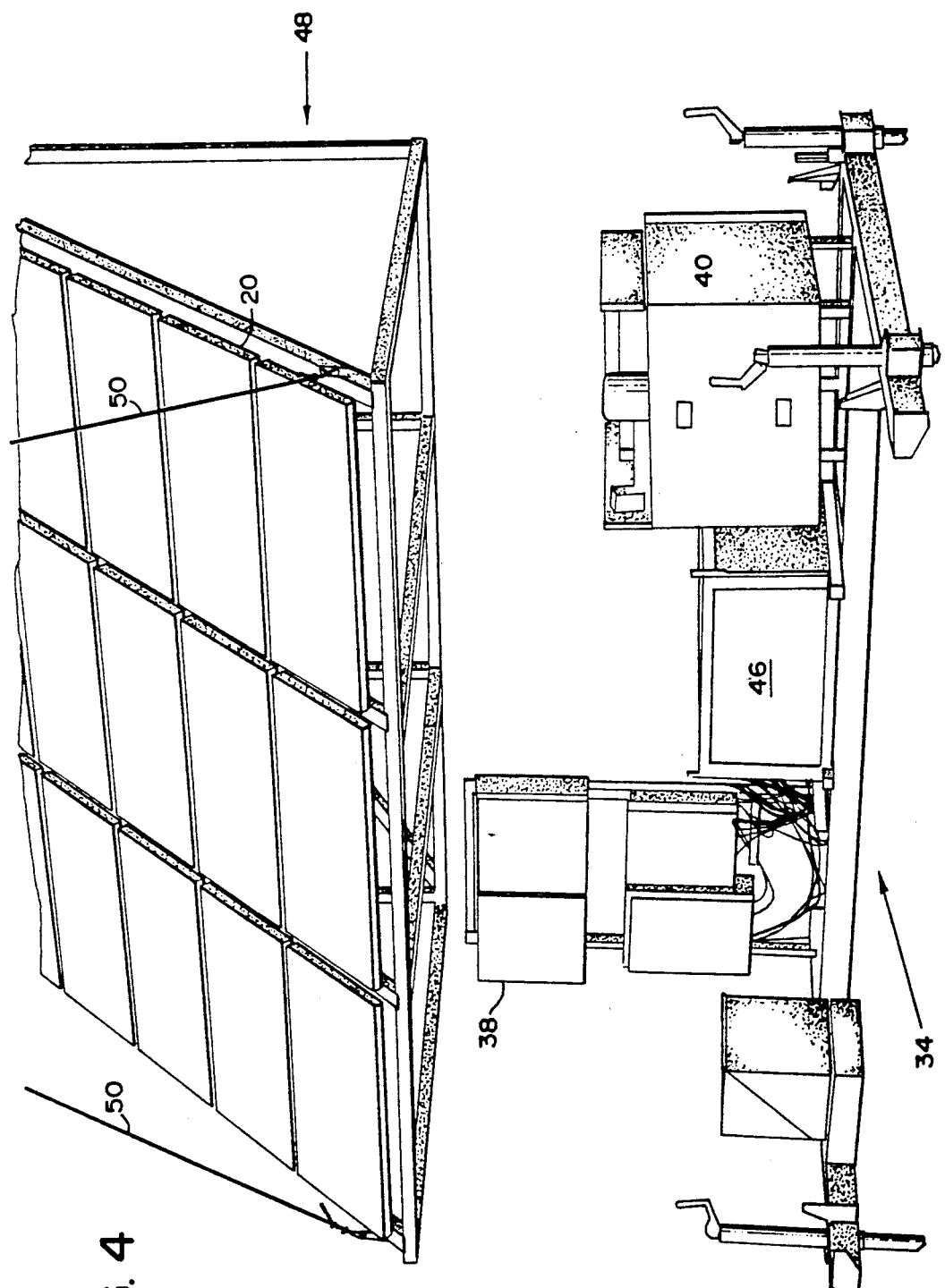
FIG. 4 is a perspective view of the solar array skid in the process of being lowered by helicopter or crane on to the instrument skid with the battery skid already mounted thereon.

In FIG. 4, the solar array skid, generally indicated at 48, is shown being lowered onto the instrument skid 34, guided by three technicians, and suspended by a crane or a helicopter via cables 50.

Figure 5:
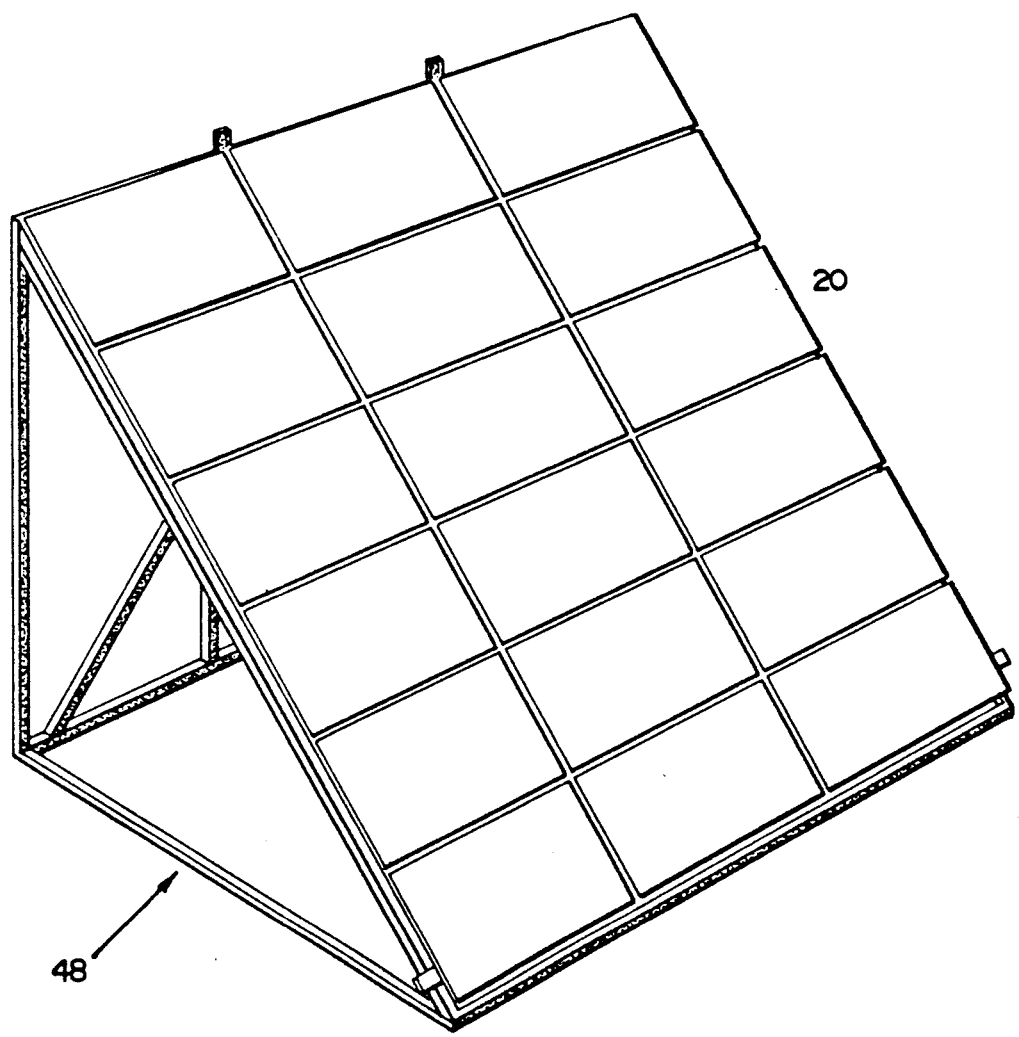
FIG. 5 is an isometric view of the solar array skid.
Figure 6:
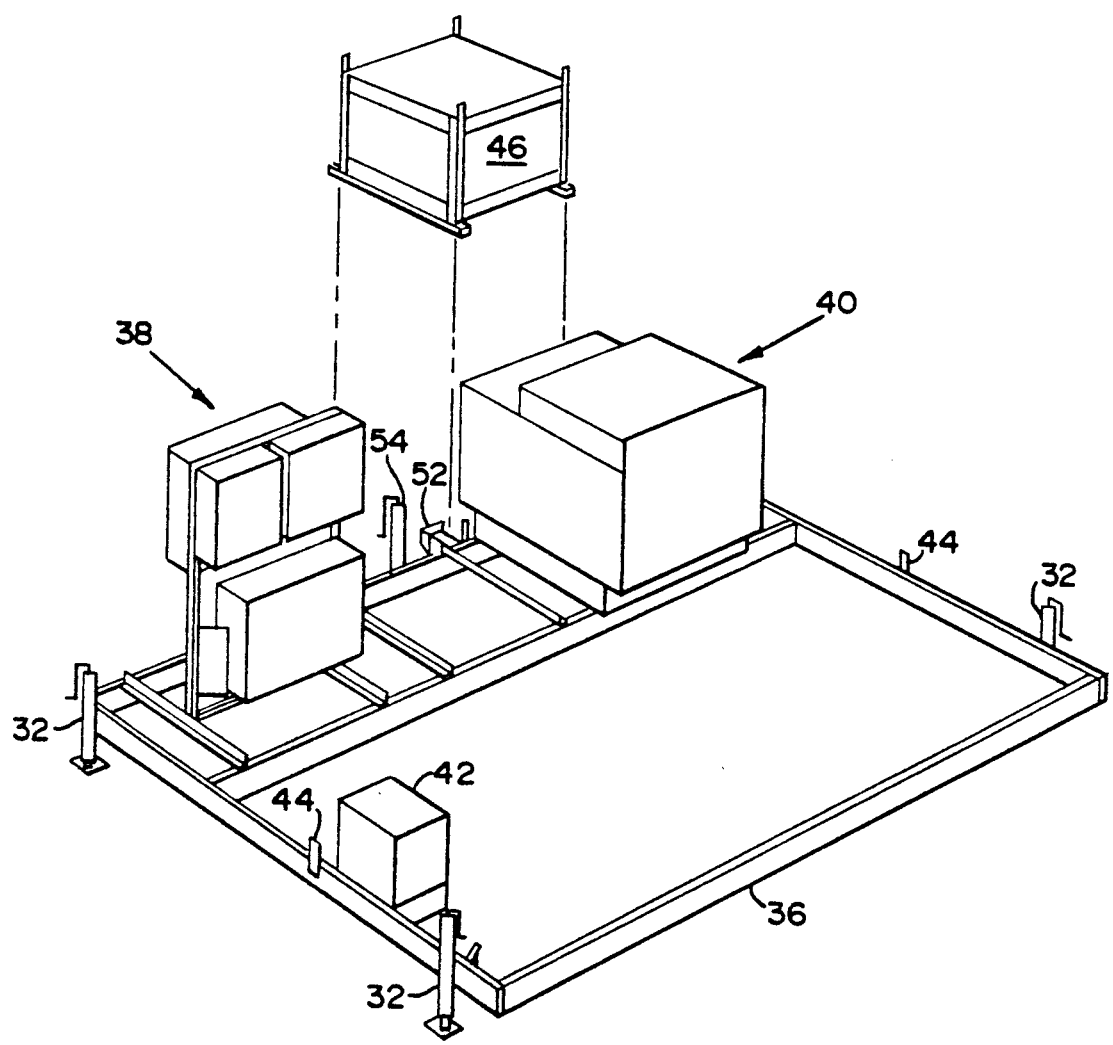
FIG. 6 is an isometric view of the battery skid and instrument skid with the dotted lines in FIGS. 5 and 6 showing how assembly may be effected by crane or helicopter.

FIGS. 5 and 6 illustrate how the instrument skid 34, battery skid 46, and solar array skid 48 fit together at the site. As will be described in greater detail later, the solar array skid 48 is guided by the jacks 32 at the four corners of the instrument skid 34 as it is lowered onto the instrument skid 34. A number of vertically disposed plates 52 mounted to the rear, end of the instrument skid 34, guide the rear side of the solar array skid 48. The instrument skid 34 and solar array skid are suitably affixed together as by bolts.

Previous to mounting the solar array skid 48, a fifth jack 54 located next to the battery skid is lowered to help support its weight.

Figure 7:
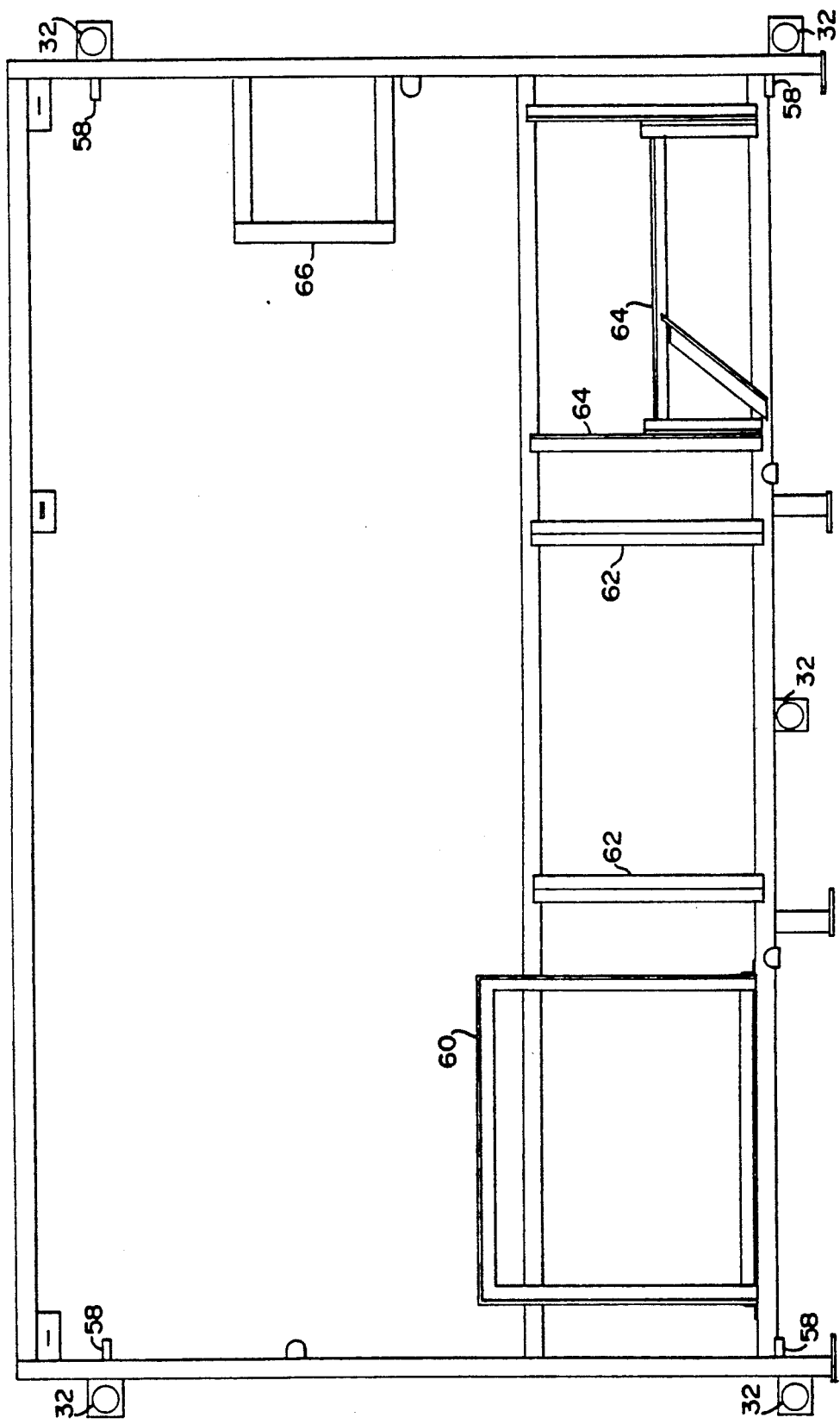
FIG. 7 is a top view of the instrument skid of the invention.
Figure 8:
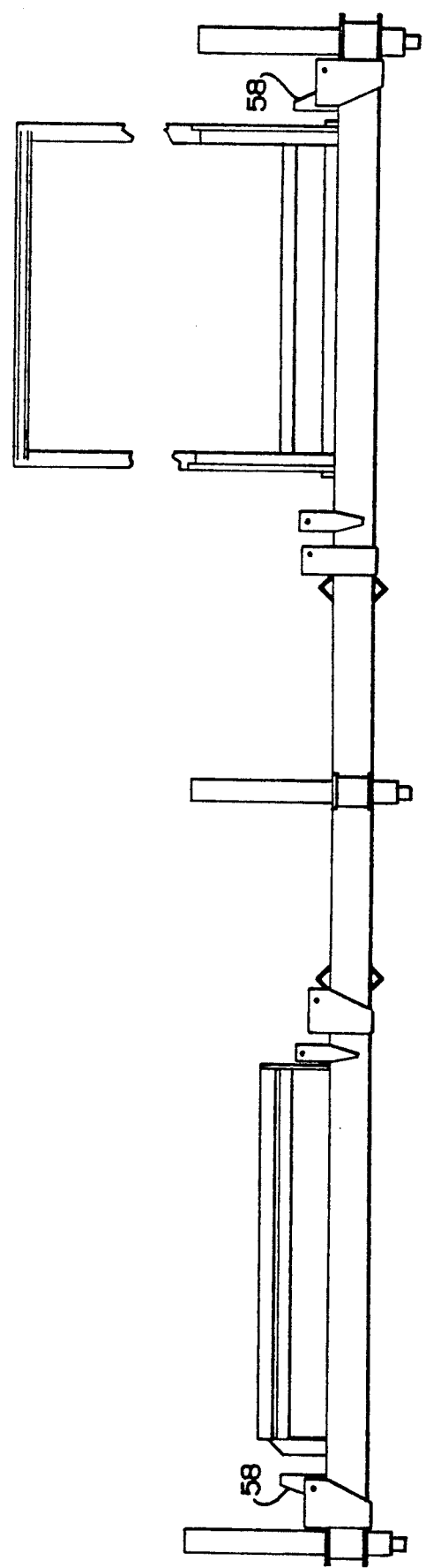
FIG. 8 is a front view from the equator of the instrument skid of the invention.

FIG. 7 shows the frame 36 of the instrument skid 34 in some detail. The four lifting eyes 44 can be seen to be placed at the apexes of a trapezoid, such that the center of gravity of the instrument skid 34 is well within the sides of the trapezoid for stability in lifting. Front member 56, in some instances can be omitted to save weight, as shown in FIGS. 2, 3, and 4. Four inclined guides 58 are provided. The guide 58, nearest to the equator, can best be seen in FIG. 4 and the guide 58, farthest from the equator, can best be seen in FIG. 8. The frame 60, for holding the gas analyzer can best be seen in FIG. 7, as can rail 62 for holding the battery skid 46, the frame structure 64 for holding the control and instrument elements 38, and the cantilevered frame 66 for holding the generator 32.

Figure 9:
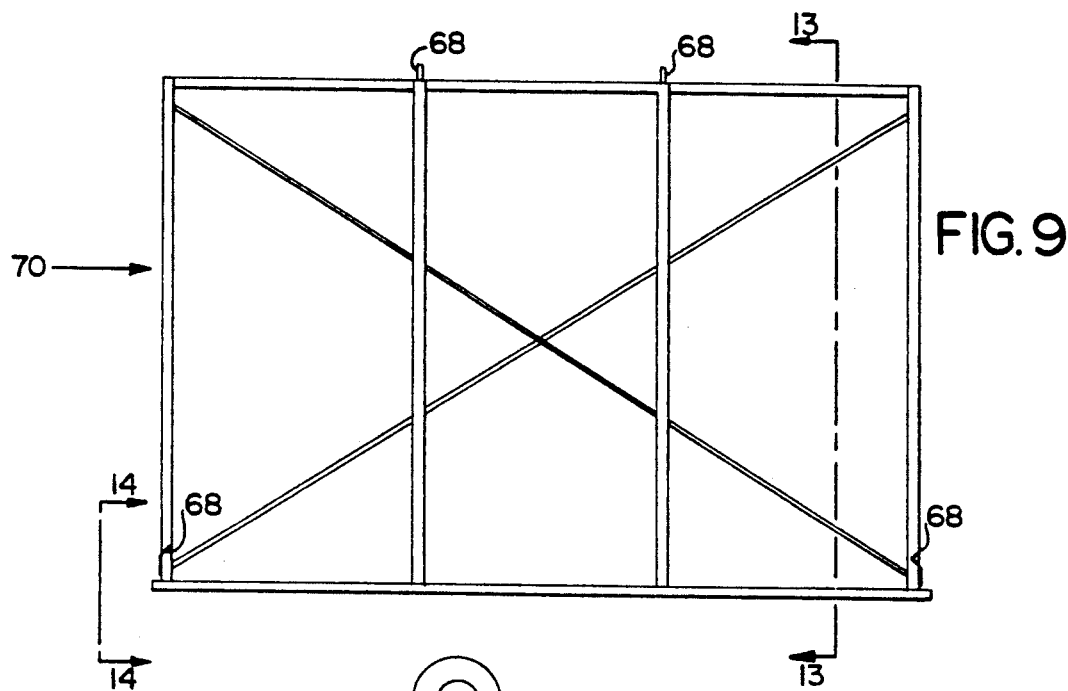
FIG. 9 is a front view from the equator of the solar array skid frame.
Figure 14:
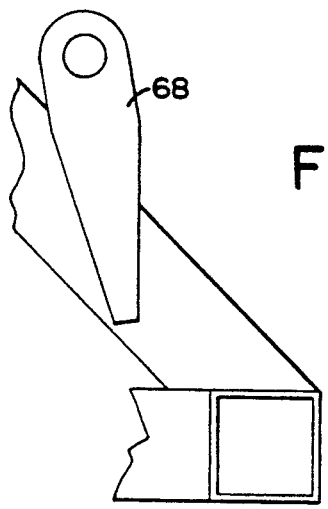
FIG. 14 is a partial view taken along the line 14—14 in FIG. 9.
Figure 10:
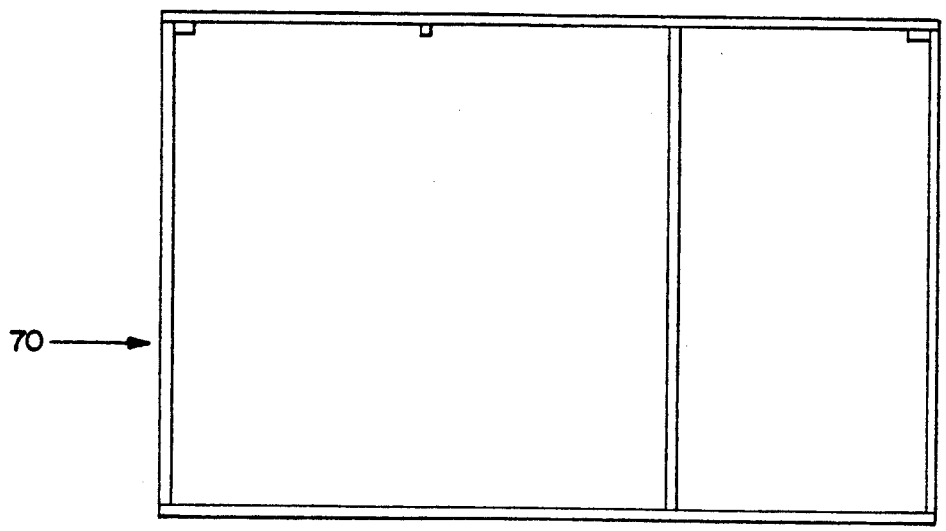
FIG. 10 is a top view of the solar array skid frame.
Figure 12:
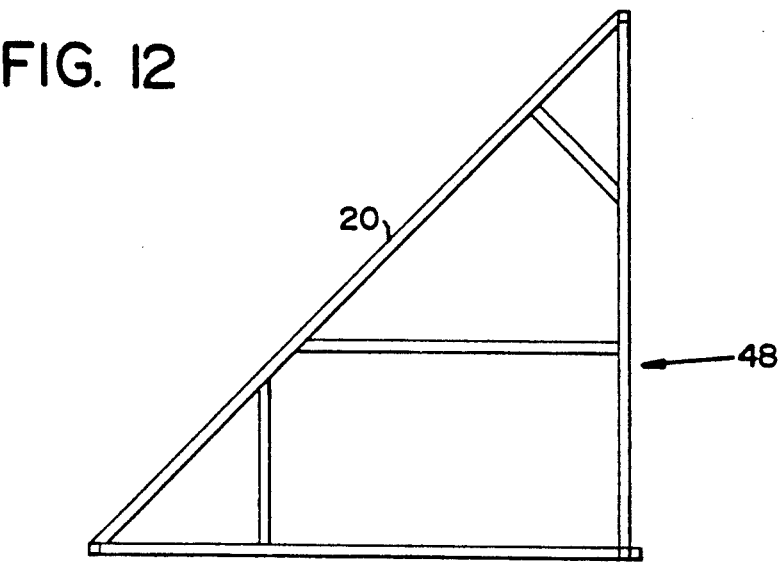
FIG. 12 is a side view of the solar array frame.
Figure 13:
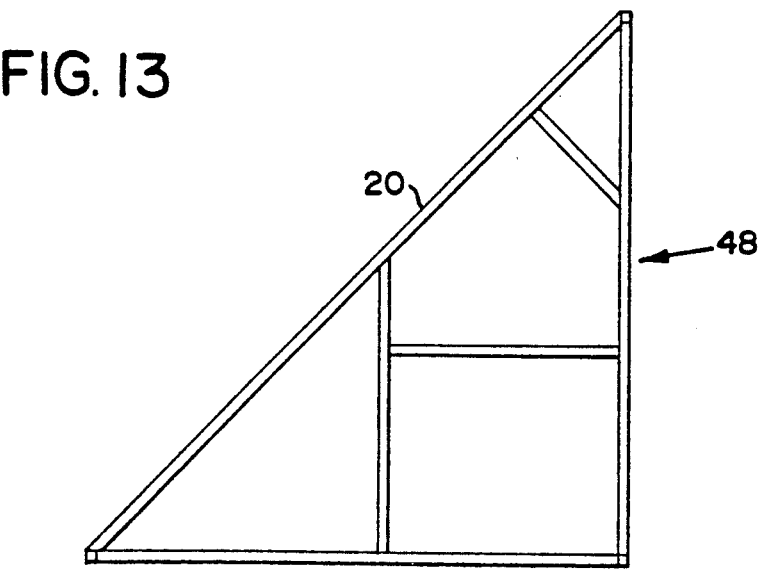
FIG. 13 is a cross-sectional view taken along the line 13—13 in FIG. 9.
Figure 15:
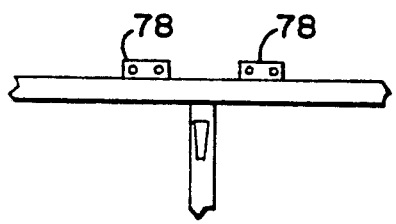
FIG. 15 is an enlarged top view taken within the circle labeled "View 15" in FIG. 11.

Now referring to FIG. 9, the four lifting eyes 68 for lifting the frame 70 of the solar array structure 48 can be seen—the detail thereof being shown in FIG. 14. The bottom view of the frame structure 70, is seen in FIG. 10, and the rear view of the frame structure 70 is shown in FIG. 11.

Figure 11:
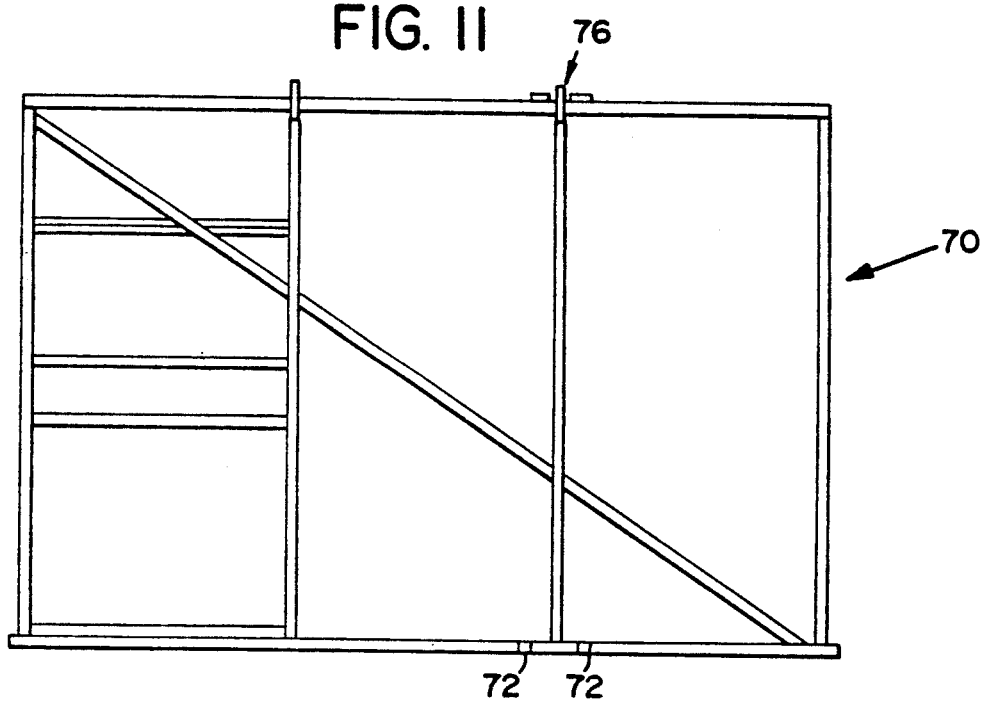
FIG. 11 is a back view toward the equator of the solar array frame.
Figure 16:
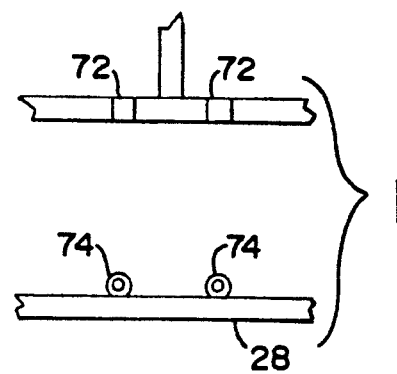
FIG. 16 is an enlarged view taken within the circle entitled "View 16" in FIG. 11.

In FIG. 11, it can be seen that holes 72-72 are provided at the bottom rear of the solar array skid into which the bottom legs, or specially provided bolts, on the mast 28 fit so that the mast is mounted to the instrument skid. The mast is also tied to the top of the solar array skid at 76 by means of a strap, not shown, and strap hangers 78-78 mounted to the top of the solar array skid so that it is solely supported on the instrumention package.

The gas analyzer intake tube 30 is also mounted to the frame 70 of the solar array skid.

Figure 17:
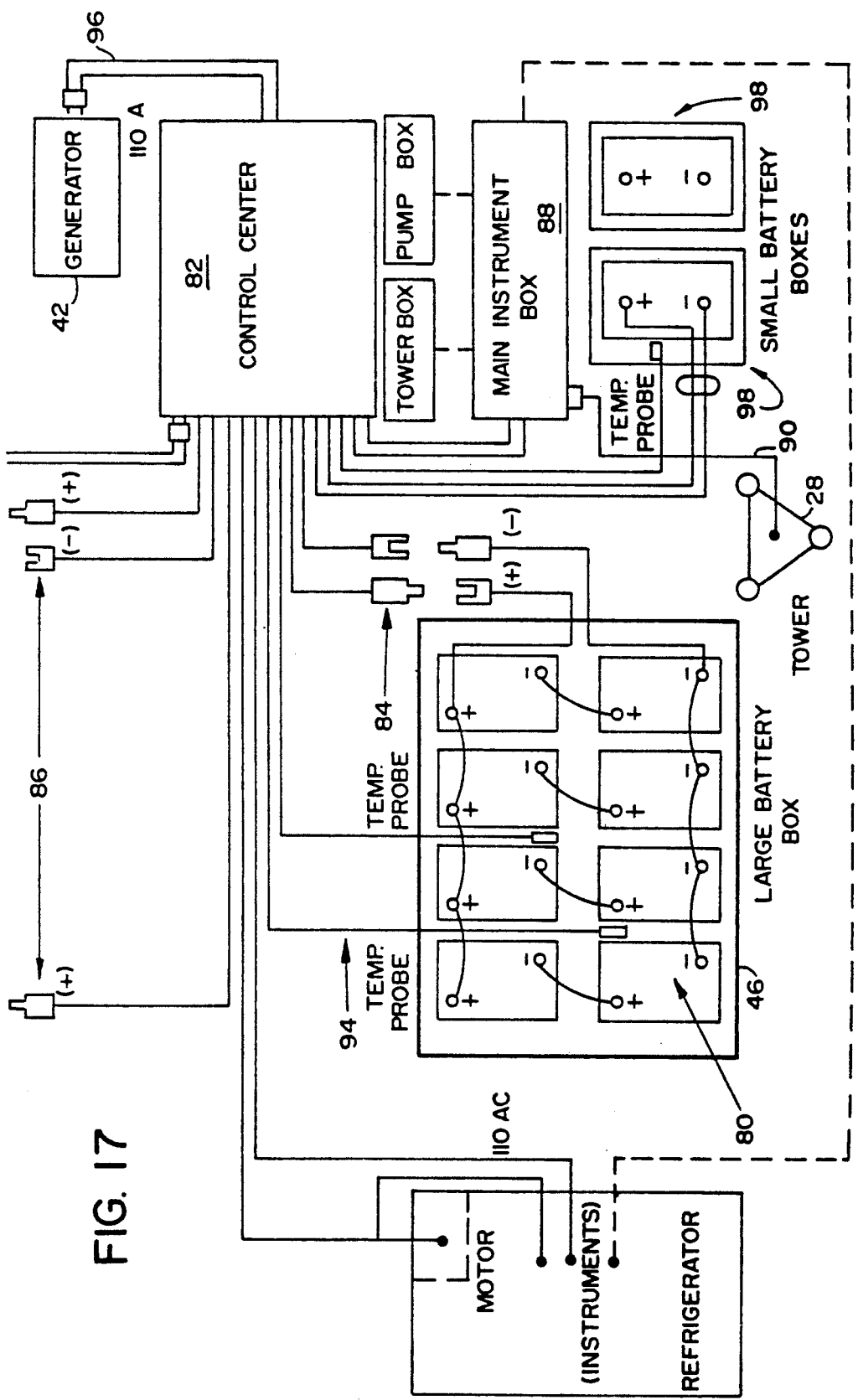
FIG. 17 is an electrical circuit diagram of an instrumentation package according to the invention; and, FIG. 18 is a diagram showing the result of north and south wind forces on the package, The same reference characters referred to the same elements throughout the several views of the drawings.

Now referring to FIG. 17, after assembly of the instrumentation package at the remote site, the batteries, generally indicated at 80, are connected to the control center 82 via two connectors, generally indicated, at 84. The solar array, which is divided into two portions, is connected via three connectors, generally indicated, at 86. The instrument array on the tower 28 is connected to the main instrument box 88 via cable 90 and connector 92. Temperature probes mounted to wires, generally indicated at 94, are inserted into the battery skid and the control center 82 is connected to the generator 42 by the 110 volt power line cord 96; the remaining wiring of the instrument and control elements having been previously effected at the factory.

The generator is turned on, the batteries initially charged, the generator turned off, and the unit immediately starts recording and, if desired, transmitting the readings at the various instruments to a data collection center.

The solar array is divided so that a small portion thereof is utilized together with the small battery boxes, generally indicated at 98, to power the instrumentation units. The large batteries 80 mounted in the battery skid 46 are utilized with the larger portion of the solar array for powering the instruments including the very large power consuming continuous gas analyzer.

Since the gas analyzer includes power consuming, heat producing units including a heater, it, when enclosed in an insulated box, can provide heating for itself in the winter; in the summer, the refrigerator cools it to its appropriate operating range. Fortunately, this exactly corresponds to the greater power output of the solar array during the summer.

An instrumentation package according to the invention has been constructed in which the weights are as follows:

| | |
|---|---|
| Battery Skid | 1,175 lbs |
| Instrument Skid | 1,125 lbs |
| Array Skid | 895 lbs |
| Array Skid w/o Tower | 790 lbs |
| Weights of components included on specific skids: | |
| Equipment on instrument skid: | |
| Generator | 63 lbs |
| Instrument Enclosure | 50 lbs |
| Instrument Box | 167 lbs |
| Equipment on Array Skid Tower: | 105 lbs |
| Equipment on Battery Skid: | 1,040 lbs |

We have carefully located the elements mounted to the instrument skid 34, in particular the very heavy battery skid 46, such that the wind velocity from the south and the wind velocity from the north which would just begin to tip the instrumentation package over, that is, lift one of the four jacks 32 from the ground, are in a predetermined ratio. The package provides much less air resistance to east and west winds and thus can sustain higher winds from those directions.

Figure 18:
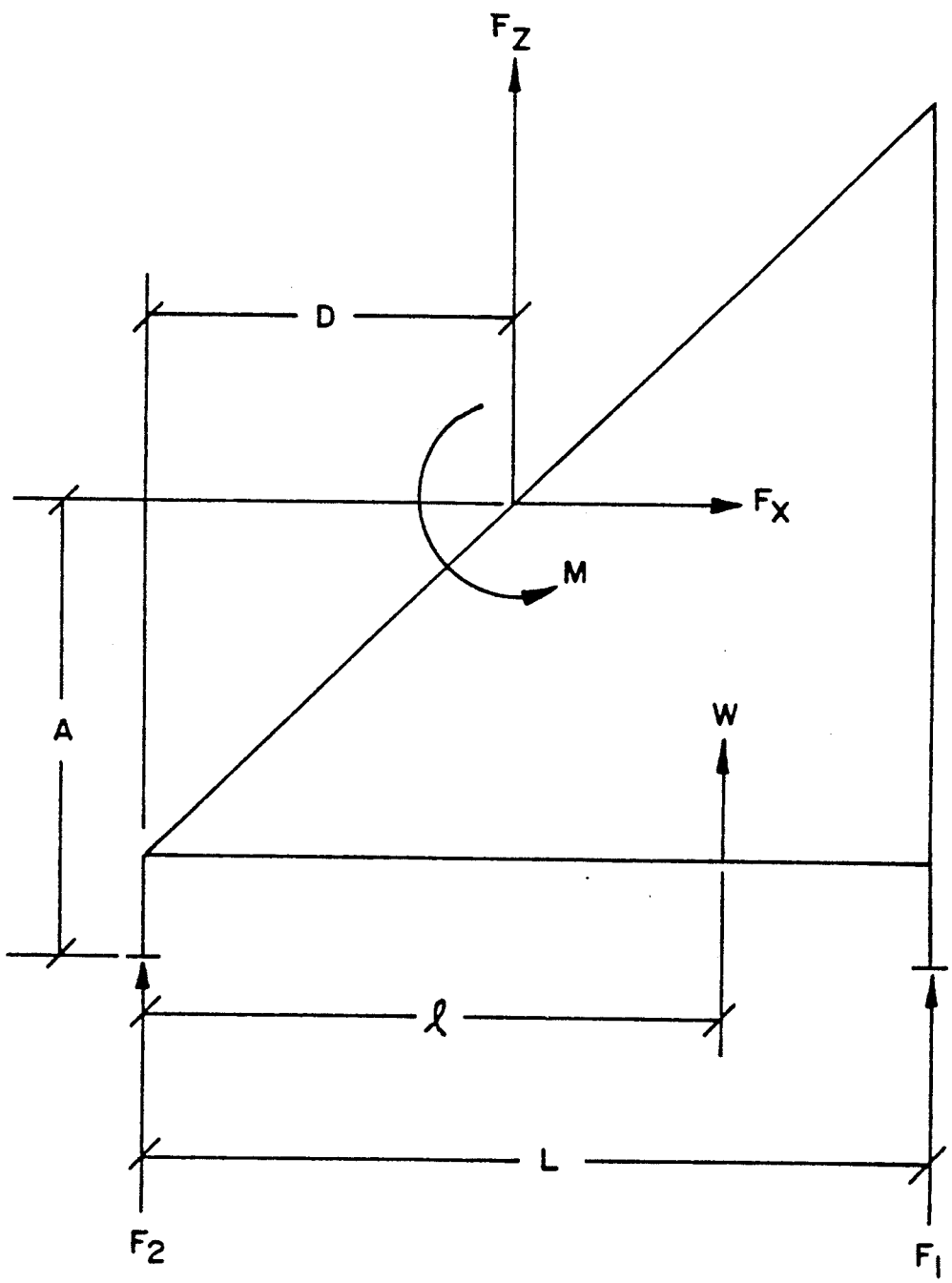

Referring to the diagram of FIG. 18 we define:

All forces and directions positive up, positive to the right; moments positive anticlockwise. By wind velocity we here intend the vector quantity, positive when blowing left to right, negative when blowing right to left. By wind speed we here mean the scalar value, regardless of direction.

Fx: Horizontal wind force
Fy: Vertical wind force
M: Aerodynamic moment
L: Horizontal distance between supports
l: Horizontal distance from left foot to Center of Gravity
A: Vertical distance from ground to aerodynamic center
d: Horizontal distance from left side to aerodynamic center
F1: Vertical force on right foot
F2: Vertical force on left foot
W: Total mass times acceleration of gravity, positive upward In the range of interest, Fx, Fy, and M are functions of wind velocity squared. The exact forms of the functions depend on the exact geometric and mechanical details of the system.

The following equations describe the net vertical force on the north and south feet. (F2 is the southern foot in the northern hemisphere, and the northern foot in the southern hemisphere.)

$$F1 = -\frac{FxA}{L} + F2(d/L) + \frac{M}{L} - W(l/L) \quad (1)$$

$$F2 = \frac{FxA}{L} + Fx(1 - d/L) - \frac{M}{L} - W(1 - l/L) \quad (2)$$

When F1 = 0:

$$l = \frac{L}{W}\left[-\frac{FxA}{L} + F2\left(\frac{d}{L}\right) + \frac{M}{L}\right] \quad (3)$$

When F2 = 0:

$$l = L\left[1 - \frac{\frac{FxA}{L} + F2(1 - d/L) - \frac{M}{L}}{W}\right]$$

When wind velocity is zero, F1 and F2 are negative, and the device is stable. As the wind velocity increases from zero, F2 increases and eventually reaches zero. At that moment, the device is in danger of, and probably will, topple. If the wind velocity decreases from zero (that is, the wind speed rises in a negative direction) F1 increases and eventually reaches zero. At that moment, the device is in danger of, and probably will, topple in the opposite direction.

Assume that winds in the range of interest are equally likely to occur from either direction. The optimum l (center of gravity) is the one at which the wind speed that causes F1 to go to zero is equal to the wind speed (in the opposite direction) that causes F2 to go to zero.

When Fx, Fy, and M can be expressed as an explicit function, the problem can be solved analytically. However, iterative and graphical solutions are also easy, and may be preferable when Fx, Fy and M cannot easily be expressed as explicit functions, as will usually be the case.

When F1 is zero (one condition of interest), Eq. 1 can be solved for l as shown at Eq. 3. When F2 is zero (the other condition of interest), Eq. 2 can be solved for l as shown at Eq. 4. Solution of the problem is achieved when the same wind speed from either direction yields the same value for l when substituted into the appropriate equation.

To solve graphically, calculate l for a series of positive wind velocities using Eq. 4 and plot l versus wind speed. Calculate l for a series of negative wind velocities using Eq. 3, and plot l versus wind speed. The two curves will intersect at the optimum l and maximum sustainable wind speed. To solve iteratively, select a starting value for the wind speed. Solve Eq. 3 and Eq. 4 for l. Using any of the many standard methods, continue varying wind speed to obtain closure of the l's obtained from each equation.

In a case where there is distinctly higher probability of high winds from one direction than the other and the probabilities are known, the method of solution is identical except that equal l's from Eq. 3 and Eq. 4 are sought not identical wind speeds, but at wind speeds weighted by probability. That is the wind speeds from the north and the south at which F1 or F2 equal zero are equally probable.

It will thus be seen that the objects set forth above, among those made apparent from the preceding description, are efficiently attained and, since certain changes may be made in the above described constructions without departing from the scope of the invention, it is intended that all matter contained in the above description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween.

Having described our invention, what we claim as new and desire to secure by Letters Patent is:

1. A helicopter installable, self-powered, modular, remote, instrumentation package comprising:
   A. an instrument skid comprising:
      a. a generally, horizontally disposed frame;
      b. instruments and control elements mounted on said frame;
      c. at least three jacks adapted to engage the ground mounted to said frame for leveling said frame;
   B. a battery skid comprising:
      a. batteries adapted to be field mounted to said instrument skid; and,
   C. a solar array skid comprising:
      a. a lean-to like structure comprising a sloped roof comprising an array of solar cells, said solar array skid being adapted for field mounting to said instrument skid;
   said battery skid and said solar array skid being adapted to be lowered onto said instrument skid in that order.

2. An instrumentation package as defined in claim 1 wherein the weight of each skid does not exceed 1,200 pounds.

3. An instrumentation package as defined in claim 1 wherein said instrument skid further comprises a self-powered electrical generator mounted thereto for transportation to a remote site.

4. An instrumentation package as defined in claim 1 wherein said battery skid is adapted to be positioned such that when said array of solar cells faces toward the equator north or south winds of predetermined relative velocity produce a zero force at any one jack.

5. The instrumentation package defined in claim 1 wherein said sloped roof of said solar array skid extends to substantially the rear edge of said instrument skid over said instruments and control elements and said battery skid.

6. The instrumentation package defined in claim 1 and:
   D. a tower mounted on said instrument skit and adapted to be fastened to said solar array skid.

7. An instrumentation package as defined in claim 1 wherein said jacks are located, so as to guide said solar array skid, when it is lowered onto said instrument skid.

8. An instrumentation package as defined in claim 1 including weather protected electrical connections between said instruments and control elements.

9. An instrumentation package as defined in claim 1 wherein said instruments comprise a gas analyzer.

10. An instrumentation package as defined in claim 9 wherein said gas analyzer is enclosed in a heat insulated refrigerated container.

* * * * *